United States Patent [19]

Mlot-Fijalkowski et al.

[11] 4,321,534

[45] Mar. 23, 1982

[54] MAGNETIC PARTICLE TESTING PROCEDURE INVOLVING PRE-COATING WITH A HYDROPHOBIC COATING

[75] Inventors: Adolf Mlot-Fijalkowski, Lincolnwood; Kenneth P. Borrows, Schaumburg, both of Ill.

[73] Assignee: Magnaflux Corporation, Chicago, Ill.

[21] Appl. No.: 129,710

[22] Filed: Mar. 12, 1980

[51] Int. Cl.³ .................. G01N 27/84; G01R 33/12
[52] U.S. Cl. ................................................. 324/216
[58] Field of Search ................ 324/214–216; 252/62.52

[56] References Cited

U.S. PATENT DOCUMENTS

| 3,345,564 | 10/1967 | Makino et al. | 324/216 |
| 3,445,759 | 5/1969 | Pevar | 324/216 |
| 3,826,917 | 7/1974 | Molina | 324/215 X |

FOREIGN PATENT DOCUMENTS

| 497408 | 12/1938 | United Kingdom | 324/216 |
| 668732 | 3/1952 | United Kingdom | 324/215 |
| 833884 | 5/1960 | United Kingdom | 324/216 |
| 667884 | 6/1979 | U.S.S.R. | 324/215 |

OTHER PUBLICATIONS

"Magnetic–Particle Inspection", *Metals Handbook,* Eighth Edition, vol. 11, pp. 55–60.

*Primary Examiner*—Gerard R. Strecker
*Attorney, Agent, or Firm*—Hill, Van Santen, Steadman, Chiara & Simpson

[57] ABSTRACT

A method for testing a magnetizable workpiece for flaws by the magnetic particle inspection method wherein a coating of finely divided, hydrophobic particles is electrostatically applied onto the surface of a workpiece to be tested after which an aqueous suspension of magnetizable particles is applied over the resulting coating. The magnetized workpiece is then inspected for deposits of magnetizable particles which have become lodged in the flaws. The hydrophobic nature of the coating repels the water from the suspension, and permits the indications to appear promptly after application of the magnetizable particle suspension.

6 Claims, No Drawings

MAGNETIC PARTICLE TESTING PROCEDURE INVOLVING PRE-COATING WITH A HYDROPHOBIC COATING

BACKGROUND OF THE INVENTION

1. Field of the Invention

This invention is in the field of non-destructive testing, particularly non-destructive testing methods employing magnetizable particles which may also have the characteristic of fluorescing under ultraviolet irradiation. The specific improvement of the present invention is directed to the application of a light, fluffy hydrophobic coating onto the surface of the workpiece prior to application of an aqueous suspension of magnetizable particles whereby the particles are retained in flaws on the magnetized workpiece and the water of the suspension is shed from the surface.

2. Description of the Prior Art

Magnetic particle inspection methods have been used for flaw detection for many decades. Basically, these nondestructive testing methods includes the step of supporting a magnetizable workpiece and passing a direct or alternating current through the piece in order to magnetize the same. Contemporaneously, magnetic particles either in dry form or in suspension in water or oil are applied to the surface. The stray magnetic fields produced at any surface flaws serve to attract the magnetic particles so that they are readily visible upon inspection.

More recently, the magnetic particles have been combined with fluorescent particles either in the form of a water or oil suspension so that the workpiece is inspected under filtered ultraviolet or black light to observe any concentration pattern of fluorescent particles caused by a surface discontinuity. Prior art patents referring to this type of inspection include Switzer U.S. Pat. No. 2,267,999 and Kazenas U.S. Pat. No. 2,936,287. These patents relate, respectively, to lacquer bonded and resin bonded fluorescent magnetic particles for use in magnetic particle inspection processes.

One of the more important areas in which magnetic particle inspection is used is that of inspecting steel billets in a continuous manner. Normally, the billet is inspected for longitudinal seams and, in the case of fluorescent particles, the inspection takes place under black light in a darkened inspection area.

One of the difficulties when using the fluorescent magnetic particles in aqueous suspension is the difficulty to fix the indications on the workpiece, since the surface area remains wet for a considerable period of time. Furthermore, the background of the workpiece, such as a steel billet, tends to be slightly fluorescent in itself so that tears and other faults are poorly indicated through the use of the fluorescent magnetic particles.

SUMMARY OF THE INVENTION

In accordance with the present invention, the magnetic particle inspection method is modified by the interposition of a light, fluffy, hydrophobic coating onto the surface of the workpiece before application of the aqueous suspension containing the magnetizable particles. The term "hydrophobic" as used herein is defined in the "Concise Chemical and Technical Dictionary" (1947) as "having no affinity for water". While the invention is applicable to the use of magnetizable particles generally, it is particularly effective when used in conjunction with magnetizable particles which have the ability to fluoresce under the influence of ultraviolet light.

By far the best results have been obtained when the light, hydrophobic coating is applied by electrostatic deposition. Probably this is due to the fact that the light particles have an electrical charge of their own which causes the particles to be attracted to the oppositely charged or neutral workpiece. In any event, the light, fluffy hydrophobic particles provide an ideal surface against which fluorescent indications can be analyzed. The hydrophobic nature of the coating repels the water in the aqueous suspension carrying the magnetic particles, so that the magnetic particles deposit themselves in the pattern determined by the stray magnetic fields associated with flaws, and the water is rapidly rejected, leaving only a relatively dry surface against which the indications can be analyzed. The presence of the intermediate coating also eliminates any background fluorescence which sometimes occurred when fluorescent type magnetic particles were applied directly over a steel surface.

DESCRIPTION OF THE PREFERRED EMBODIMENTS

Basically, the present invention involves precoating of workpieces such as steel billets with a normally white, hydrophobic extremely light and fluffy powder, allowing the formation of fluorescent indications from water suspension while leaving the entire surface area free of water. Because the inspecting surface is substantially water free, the fixation of indications becomes relatively easy. Instead of drying the whole billet, which was a technique previously used after application of the aqueous suspension, only a minimal amount of heat is required to dry the formed indication. This usually can be accomplished by means of a gentle stream of warm air. The uniform powder coating which normally ranges from a gray to a white color depending on the film thickness eliminates any glare which has previously been troublesome in connection with metallic surfaces. Furthermore, the whiteness of the coating provides a superior background for the fluorescent type magnetic particles which usually fluoresce in the orange or red range. Tears and other faults which have previously been poorly indicated by fluorescent magnetic particles now stand out very well against the non-fluorescent background.

In a particularly preferred form of the present invention, we make use of the type of improved fluorescent magnetic powders described in Borrows U.S. Ser. No. 94,764, filed Nov. 16, 1979, and assigned to the same assignee as the present application. In the aforementioned copending application there is described a composition for non-destructive testing of magnetizable workpieces employing discrete magnetic particles having a ferromagnetic particle core, fluorescent pigment particles attached to the core, and a cascading opacifier associated with the core, the fluorescent pigment particles being at least 2 microns in maximum dimension. In the preferred form of the invention, the cascading opacifier is fluoranthene, and the core particles have a maximum dimension of from 25 to 150 microns. The core particles and daylight fluorescent pigment particles are held together by means of encapsulation with a film-forming resin which also serves as the carrier for the opacifier.

The magnetic particles are applied in the form of an aqueous suspension. Such suspensions are well known in the prior art and usually involve the use of from 0.05 to 1 ounce of fluorescent magnetic particles per gallon of water. The suspension can also include surfactants and other additives.

The improved hydrophobic coating of the present invention consists of very finely divided, fluffy extremely light particles such as those available commercially under the following trademarks:

Degussa "D-17"
"Aerosil R972"
"Tullanox 292"
"Tullanox A-50"
"Titanium Dioxide P-25".

The Degussa "D-17" is a silica aerogel in which substantially all of the particles are less than 100 nanometers (millimicrons) in maximum dimension, and the average primary particle size is about 18 nanometers. It has a bulk density of about 80 grams per liter.

The "Aerosil R972" is also a silica aerogel having an average primary particle size of 16 nanometers. It has a tamped density as measured by the test procedure DIN 53 194 of approximately 50 grams per liter.

The "Tullanox 292" is a powdered fumed silica having an extremely high surface area which has been modified by reaction with an organic silicone. The hydrophilic hydroxyl groups which normally appear on the silica surface are partially replaced with organic trimethyl silyl groups. This material has a bulk density of about 3.0 pounds per cubic foot.

The "Tullanox A-50" is a hydrophobic precipitated silica having a nominal particle size of about 18 nanometers and a bulk density of about 8 pounds per cubic foot.

The "Titanium Dioxide P-25" is marketed by Degussa and has a primary particle size of from 15 to 40 nanometers.

The hydrophobic, fluffy powders can be easily applied by means of standard electrostatic spraying procedures. Electrostatic spray guns suitable for applying electrically non-conductive finely divided powders are readily available on the market.

Electrostatic coating of the hydrophobic powder produces a uniformly white coating on the surface of a steel billet. In a specific example, the hydrophobic powder "D-17" was sprayed electrostatically several times on a steel billet. There was no difficulty in applying the powder uniformly. A suspension of fluorescent magnetic particles in an amount of 1/5-ounce per gallon of water was poured over the area, and indications appeared immediately while the excess water drained off promptly. A dry coating of the hydrophobic powder resulted against which the deposits of fluorescent magnetic particles could be readily analyzed upon irradiation with ultraviolet light.

It should be evident that various modifications can be made to the described embodiments without departing from the scope of the present invention.

We claim as our invention:

1. A method for testing a magnetizable workpiece for flaws which comprises:

magnetizing said workpiece, electrostatically applying a coating of finely divided, hydrophobic particles onto the surface of said workpiece, applying an aqueous suspension of magnetizable particles over the resulting coating, said coating having the property of repelling the water in said aqueous suspension, and inspecting said surface for magnetizable particles which have become lodged in said flaws against the background of said coating.

2. A method according to claim 1 in which:

said magnetizable particles are capable of fluorescing when exposed to ultraviolet irradiation, and said inspecting is done under ultraviolet light.

3. A method according to claim 1 in which substantially all of said hydrophobic particles have a particle size below 100 nanometers.

4. A method according to claim 1 in which said hydrophobic particles are composed of titanium dioxide.

5. A method according to claim 1 in which said hydrophobic particles are composed of a silica aerogel.

6. A method according to claim 1 in which said hydrophobic particles are composed of a fumed silica.

* * * * *